US011007474B2

(12) United States Patent
Bao

(10) Patent No.: US 11,007,474 B2
(45) Date of Patent: May 18, 2021

(54) SYSTEM AND METHOD USED TO RECYCLE EXHAUST GAS DURING OLEFIN POLYMER PRODUCTION

(71) Applicant: HANGZHOU OUYUAN TECHNOLOGY CO., LTD, Zhejiang (CN)

(72) Inventor: Chonglong Bao, Zhejiang (CN)

(73) Assignee: HANGZHOU OUYUAN TECHNOLOGY CO., LTD, Hangzhou (CN)

( * ) Notice: Subject to any disclaimer, the term of this patent is extended or adjusted under 35 U.S.C. 154(b) by 103 days.

(21) Appl. No.: 16/432,978

(22) Filed: Jun. 6, 2019

(65) Prior Publication Data

US 2019/0282955 A1    Sep. 19, 2019

Related U.S. Application Data

(63) Continuation of application No. PCT/CN2017/080634, filed on Apr. 14, 2017.

(30) Foreign Application Priority Data

Dec. 7, 2016    (CN) .......................... 201611113322.2

(51) Int. Cl.
*B01D 53/22*    (2006.01)
*B01D 53/00*    (2006.01)
(Continued)

(52) U.S. Cl.
CPC .......... *B01D 53/229* (2013.01); *B01D 53/00* (2013.01); *B01D 53/002* (2013.01); *B01D 53/226* (2013.01); *B01D 53/228* (2013.01); *C01B 21/0433* (2013.01); *C01B 21/0444* (2013.01); *C07C 7/005* (2013.01); *C07C 7/144* (2013.01);

(Continued)

(58) Field of Classification Search
USPC ....................... 96/7; 585/809, 818
See application file for complete search history.

(56) References Cited

U.S. PATENT DOCUMENTS

| 6,559,348 B1 * | 5/2003 | Aittamaa | ............. B01D 53/229 |
| | | | 203/39 |
| 9,034,995 B2 * | 5/2015 | Yang | ........................ C08F 6/001 |
| | | | 526/61 |
| 2017/0008822 A1 * | 1/2017 | Wynn | ..................... B01D 53/22 |

FOREIGN PATENT DOCUMENTS

| CN | 102161715 B | 8/2011 |
| CN | 102389643 A | 3/2012 |

(Continued)

OTHER PUBLICATIONS

International search report of PCT Patent Application No. PCT/CN2017/080634 dated Sep. 13, 2017.

*Primary Examiner* — Fred M Teskin

(57) ABSTRACT

A system used to recycle exhaust gas during olefin polymer production, comprising: a compression cooling mechanism (101); a hydrocarbon membrane separation mechanism (102) and a hydrogen membrane separation mechanism (103), both connected to a first outlet (202) of the compression cooling mechanism; and a deep cooling mechanism (104) connected to a first outlet (208) of the hydrogen membrane separation mechanism. A method used to recycle exhaust gas during olefin polymer production, comprising a compression cooling step, a hydrocarbon membrane separation step, a hydrogen membrane separation step and a deep cooling step.

17 Claims, 1 Drawing Sheet

(51) Int. Cl.
*C01B 21/04* (2006.01)
*C07C 7/00* (2006.01)
*C07C 7/144* (2006.01)
*F25J 3/02* (2006.01)

(52) U.S. Cl.
CPC ........... *F25J 3/0219* (2013.01); *F25J 3/0238* (2013.01); *F25J 3/0257* (2013.01); *F25J 2205/10* (2013.01); *F25J 2205/80* (2013.01); *F25J 2240/02* (2013.01); *Y02P 20/129* (2015.11)

(56) References Cited

FOREIGN PATENT DOCUMENTS

| | | |
|---|---|---|
| CN | 202485331 U | 10/2012 |
| CN | 103520946 A | 1/2014 |

* cited by examiner

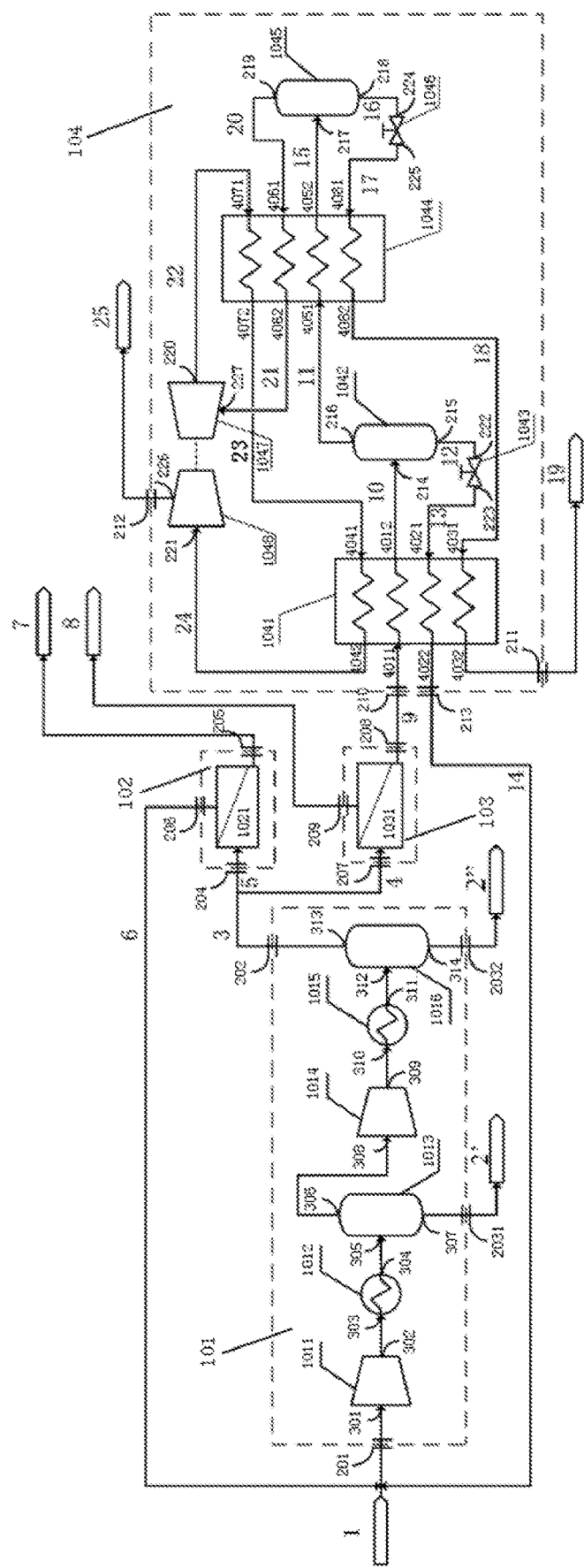

SYSTEM AND METHOD USED TO RECYCLE EXHAUST GAS DURING OLEFIN POLYMER PRODUCTION

CROSS-REFERENCE TO RELATED APPLICATIONS

This application is a Continuation Application of PCT/CN2017/080634 filed on Apr. 14, 2017, which claims the priority of Chinese patent application No. 201611113322.2, entitled "System and Method Used to Recycle Exhaust Gas During Olefin Polymer Production" and filed on Dec. 7, 2016. The entirety of the above applications is incorporated herein by reference.

FIELD OF THE INVENTION

The present invention relates to the technical field of tail gas treatment, and in particular, to a system and a method for recycling an exhaust gas in olefin polymer production.

BACKGROUND OF THE INVENTION

In a process of olefin polymer production, unreacted hydrocarbon substances (ethylene, ethane, propylene, butylene, butane, isopentane, hexene, etc.), nitrogen gas, hydrogen gas, remaining catalysts and so on are dissolved in polyolefin resin discharged from a reaction system. These unreacted hydrocarbons and the hydrogen gas must be removed, and residual catalysts in the polyolefin resin must be deactivated so as to meet environmental protection standards and to ensure safety of downstream processes and products. Therefore, the polyolefin resin needs to be devolatilized so as to obtain a qualified product. An exhaust gas produced in a devolatilization process contains a large amount of hydrocarbon components. If the exhaust gas is directly discharged to a flare system for burning without being recycled, it will cause serious waste of raw materials and economic loss, and meanwhile it will cause environmental pollution and fail to meet a specified emission index. Therefore, exhaust gas recycling is an important process step in the olefin polymer production process.

The compression condensation method is a traditional gas separation process, which achieves gas separation by utilization of a difference in dew points of respective components in the exhaust gas. The compression condensation method has a simple process and a large processing amount, and has been widely used in polyolefin exhaust gas recycling. The compression condensation method mainly has the following disadvantages: the lower a content of condensable hydrocarbons in the exhaust gas is, the lower efficiency of the compression condensation method is; and it is difficult to recycle C1-C3 hydrocarbons whose boiling point is close to that of the nitrogen gas which is a purge gas, and a recycling rate of the C1-C3 hydrocarbons is generally not more than 30%. If it is desired to further improve the recycling rate of hydrocarbon components, it is needed to use a normal temperature refrigeration ice machine to input cooling energy to a recycling system to achieve a lower temperature in the recycling system, and a commonly used temperature is −10 to 35° C. If it is desired to further reduce the temperature, it is needed to use a cascade refrigeration ice machine or a mixed refrigerant refrigeration ice machine. However, a refrigeration ice machine requires relatively large investment, and an ice machine refrigeration system has high energy consumption and poor operation stability.

In the pressure swing adsorption method, monomers in a polyolefin exhaust gas are recycled by utilization of a physical absorption-desorption process. The pressure swing adsorption method is generally used in combination with the compression condensation method, and is arranged to follow a compression condensation section. Although the pressure swing adsorption method can further recycle the hydrocarbons based on the compression condensation method, the pressure swing adsorption method has complicated procedures and a large number of devices. Moreover, pressurizing and depressurizing in a great deal of absorption towers repeatedly require extra energy consumption and utilities, resulting in a significant increase in operating costs and investment.

For many gas phase polyethylene apparatuses at home and abroad, a membrane separation device has been added for separation and recycling of the exhaust gas. Patent CN202485331U discloses a method for recycling of a film separation tail gas. In this method, hydrocarbons are further recycled by a deep cooling manner on the basis of recycling of hydrocarbon substances in a membrane system, and this method is characterized in that pressure of the tail gas is used to perform work through a turbo expander to achieve a low temperature required for condensing light components such as ethylene. However, this method cannot be combined with the devolatilization process of a polyolefin technology in a satisfactory manner. For example, the tail gas discharged in this method has low pressure, and cannot be further recycled. Besides, for the case of a high content of a hydrogen gas, recycling of the purge gas may cause accumulation of the hydrogen gas in the system, resulting in a series of problems such as a decrease in recycling efficiency.

Patent CN102161715B discloses a method for degassing a solid polymer and recycling an effluent gas. In this method for recycling the effluent gas, a gas membrane separation device is arranged to follow a compression condensation device, and the method for recycling the effluent gas is characterized in that high pressure of the effluent gas after compression is used to remove a small molecule gas or to further recycle a solvent and unreacted monomers in an uncondensed gas by the membrane separation device. By using this method, more than 95% of the solvent and the unreacted monomers can be recycled, and meanwhile recycling of a degassing medium can be realized. In this way, more than 5% energy can be saved by this method than by a conventional effluent gas recycling method.

Although recycling of hydrocarbons and nitrogen gas can be realized in the above methods, the following problems cannot be solved: the compression condensation device requires a normal temperature refrigeration ice machine as refrigeration equipment; and maintenance of power equipment is difficult, and the power equipment has high investment cost, affects operation stability, and increases separation energy consumption. Therefore, it has great economic benefits and practical significance to invent a system and a method for recycling a polyolefin exhaust gas which can efficiently recycle respective components in the exhaust gas and avoid using the ice machine as the refrigeration equipment.

SUMMARY OF THE INVENTION

The technical problem to be solved by the present invention is to provide a system for recycling an exhaust gas in olefin polymer production with respect to deficiencies in the existing technologies. This system can efficiently recycle hydrocarbon substances in the exhaust gas, effectively separate hydrocarbons and a nitrogen gas, improve purity and a recycling rate of the nitrogen gas, and a recycled exhaust gas can be returned to a resin devolatilization device for reuse. Meanwhile, using an ice machine as refrigeration equipment is successfully avoided, which effectively reduces equipment maintenance cost and ensures stable operation of a subsequent separation device.

The present invention also provides a method for recycling an exhaust gas in olefin polymer production. In this method, there is no need to use the ice machine as the refrigeration equipment, so that low energy consumption, low investment cost, and high economic benefits can be achieved; and moreover, hydrocarbon substances in the exhaust gas can be efficiently recycled, and purity and a recycling rate of a nitrogen gas can be improved, which is environment friendly and free of contamination.

For this purpose, a system for recycling an exhaust gas in olefin polymer production is provided according to a first aspect of the present invention. The system comprises:

a compression cooling mechanism;

a hydrocarbon membrane separation mechanism and a hydrogen membrane separation mechanism, both connected to a first outlet of the compression cooling mechanism; and a deep cooling mechanism connected to a first outlet of the hydrogen membrane separation mechanism.

In some embodiments of the present invention, the compression cooling mechanism comprises at least one compression cooling unit, wherein the compression cooling unit comprises a compressor, a first heat exchanger, and a first gas-liquid separator, wherein the compressor, the first heat exchanger, and the first gas-liquid separator are connected in series.

In some embodiments of the present invention, the deep cooling mechanism comprises at least one deep cooling unit, wherein the deep cooling unit comprises a second heat exchanger, a second gas-liquid separator, a first throttle valve, a third heat exchanger, a third gas-liquid separator, a second throttle valve, a turbo expander, and a turbo expander pressurization end.

According to the present invention, when the deep cooling mechanism comprises one deep cooling unit, a first inlet of the second heat exchanger is connected to an inlet of the deep cooling mechanism, and a first outlet of the second heat exchanger is connected to an inlet of the second gas-liquid separator, a gas phase outlet of the second gas-liquid separator being connected to a first inlet of the third heat exchanger, a first outlet of the third heat exchanger being connected to an inlet of the third gas-liquid separator, a gas phase outlet of the third gas-liquid separator being connected to a second inlet of the third heat exchanger, a second outlet of the third heat exchanger being connected to an inlet of the turbo expander, an outlet of the turbo expander being connected to a third inlet of the third heat exchanger, a third outlet of the third heat exchanger being connected to a fourth inlet of the second heat exchanger, a fourth outlet of the second heat exchanger being connected to an inlet of the turbo expander pressurization end, an outlet of the turbo expander pressurization end being connected to a second outlet of the deep cooling mechanism;

a liquid phase outlet of the second gas-liquid separator is connected to an inlet of the first throttle valve, and an outlet of the first throttle valve is connected to a second inlet of the second heat exchanger, a second outlet of the second heat exchanger being connected to an inlet of the compression cooling mechanism; and a liquid phase outlet of the third gas-liquid separator is connected to an inlet of the second throttle valve, and an outlet of the second throttle valve is connected to a fourth inlet of the third heat exchanger, a fourth outlet of the third heat exchanger being connected to a third inlet of the second heat exchanger, a third outlet of the second heat exchanger being connected to a first outlet of the deep cooling mechanism.

In some embodiments of the present invention, a second outlet of the hydrocarbon membrane separation mechanism is connected to an inlet of the compression cooling mechanism.

According to some embodiments of the present invention, cooling mediums used in the system all have a temperature not lower than an ambient temperature.

A method for recycling an exhaust gas in olefin polymer production by using a system as described in the first aspect is provided according to a second aspect of the present invention. The method comprises:

a compression cooling step, wherein after an olefin polymer exhaust gas is fed into a compression cooling mechanism, the olefin polymer exhaust gas is processed by a compression cooling unit to form a remaining exhaust gas stream which is outputted via a first outlet of the compression cooling mechanism, and a $C_4^+$ high carbon hydrocarbon stream as a liquid phase which is outputted via a second outlet of the compression cooling mechanism, and the remaining exhaust gas stream is fed into a hydrocarbon membrane separation mechanism;

a hydrocarbon membrane separation step, wherein the remaining exhaust gas stream fed into the hydrocarbon membrane separation mechanism is processed by a hydrocarbon membrane module to form a product discharge system (PDS) transport gas stream which is outputted via a first outlet of the hydrocarbon membrane separation mechanism, and a $C_4^+$ high carbon hydrocarbon stream which is outputted via a second outlet of the hydrocarbon membrane separation mechanism, and the remaining exhaust gas is fed into a hydrogen membrane separation mechanism;

a hydrogen membrane separation step, wherein the remaining exhaust gas fed into the hydrogen membrane separation mechanism is processed by a hydrogen membrane module to form a remaining tail gas stream which is outputted via a first outlet of the hydrogen membrane separation mechanism, and a mixed non-condensable gas stream containing hydrogen gas which is outputted via a second outlet of the hydrogen membrane separation mechanism, and the remaining tail gas stream is fed into a deep cooling mechanism; and a deep cooling step, wherein the remaining tail gas stream fed into the deep cooling mechanism is processed by a deep cooling unit to form a nitrogen gas stream which is outputted via a first outlet of the deep cooling mechanism, a $C_2^+$ low carbon hydrocarbon stream which is outputted via a second outlet of the deep cooling mechanism, and a $C_4^+$ high carbon hydrocarbon stream which is outputted via a third outlet of the deep cooling mechanism.

In some embodiments of the present invention, a volume ratio of the remaining exhaust gas stream fed into the hydrocarbon membrane separation mechanism to the remaining exhaust gas stream fed into the hydrogen membrane separation mechanism is 0.1 to 0.8; preferably, the volume ratio of the remaining exhaust gas stream fed into the hydrocarbon membrane separation mechanism to the remaining exhaust gas stream fed into the hydrogen membrane separation mechanism is 0.4 to 0.6; and further preferably, the volume ratio of the remaining exhaust gas stream fed into the hydrocarbon membrane separation mechanism to the remaining exhaust gas stream fed into the hydrogen membrane separation mechanism is 0.45 to 0.55.

In other embodiments of the present invention, the $C_4^+$ high carbon hydrocarbon stream outputted via the second outlet of the hydrocarbon membrane separation mechanism is returned to the compression cooling mechanism.

In other embodiments of the present invention, the $C_4^+$ high carbon hydrocarbon stream outputted via the third outlet of the deep cooling mechanism is returned to the compression cooling mechanism.

Compared with existing technologies, the present invention has the following advantages. The system and method for recycling an exhaust gas in olefin polymer production in the present invention, by a combination of a compression cooling mechanism, a hydrocarbon membrane separation mechanism, a hydrogen membrane separation mechanism, and a deep cooling mechanism, can efficiently recycle hydrocarbon substances in the exhaust gas, effectively separate hydrocarbons and a nitrogen gas, improve purity and a recycling rate of the nitrogen gas, and a recycled exhaust gas can be returned to a resin devolatilization device for reuse. Meanwhile, using an ice machine as refrigeration equipment is successfully avoided, and a deep cooling mechanism requiring no external energy is used to separate the nitrogen gas, $C_2^+$ hydrocarbons and $C_4^+$ hydrocarbons, which effectively reduces equipment maintenance cost and ensures stable operation of a subsequent deep cooling mechanism. Moreover, the system and the method have low energy consumption, low investment cost, and high economic benefits, and are environment friendly and free of contamination.

BRIEF DESCRIPTION OF THE DRAWINGS

The present invention will be described below with reference to the accompanying drawings, in which:

The sole FIGURE schematically shows a structure of a system for recycling an exhaust gas in olefin polymer production according to an embodiment of the present invention.

In the accompanying drawing, same reference signs are used for same components. The accompanying drawing is not drawn according to actual proportions.

DETAILED DESCRIPTION OF THE EMBODIMENTS

In order to make the present invention better understood, the present invention will be described below in a detailed way in combination with the embodiments and with reference to the accompanying drawings. The embodiments are only used to illustrate the present invention, rather than to limit the application scope of the present invention.

As mentioned before, for current systems used to recycle an exhaust gas during olefin polymer production, problems, such as efficient recycling of hydrocarbons and a nitrogen gas and a compression cooling device requiring a normal temperature refrigeration ice machine as refrigeration equipment, cannot be solved at the same time.

The inventors of the present invention have found through research that by a combination of a compression cooling mechanism, a hydrocarbon membrane separation mechanism, a hydrogen membrane separation mechanism, and a deep cooling mechanism, it is possible to efficiently recycle hydrocarbon substances in the exhaust gas, effectively separate hydrocarbons and a nitrogen gas, improve purity and a recycling rate of the nitrogen gas, and a recycled exhaust gas can be returned to a resin devolatilization device for reuse. Meanwhile, using an ice machine as the refrigeration equipment is successfully avoided, which effectively reduces equipment maintenance cost. The present invention is based on the above method.

For this purpose, a system for recycling an exhaust gas in olefin polymer production is provided according to a first aspect of the present invention. The system comprises:

a compression cooling mechanism;

a hydrocarbon membrane separation mechanism and a hydrogen membrane separation mechanism, both connected to a first outlet of the compression cooling mechanism; and a deep cooling mechanism connected to a first outlet of the hydrogen membrane separation mechanism.

The compression cooling mechanism is used for receiving the exhaust gas during the olefin polymer production, compressing pressures of respective gas components in the exhaust gas to a same level, and respectively outputting a recycled $C_4^+$ high carbon hydrocarbon stream and a remaining exhaust gas stream;

the hydrocarbon membrane separation mechanism is used for controlling a content of $C_4^+$ high carbon hydrocarbon in a PDS transport gas stream;

the hydrogen membrane separation mechanism is used for controlling a content of a hydrogen gas component in a remaining tail gas stream; and the deep cooling mechanism is used for receiving the remaining tail gas stream from the hydrogen membrane separation mechanism and recycling a $C_2^+$ low carbon hydrocarbon stream and a nitrogen gas stream.

In some embodiments of the present invention, the compression cooling mechanism comprises at least one compression cooling unit. The compression cooling unit comprises a compressor, a first heat exchanger and a first gas-liquid separator, and the compressor, the first heat exchanger and the first gas-liquid separator are connected in series.

In some embodiments of the present invention, an inlet of the compressor is connected to an inlet of the compression cooling mechanism, and the compressor is used for receiving the exhaust gas during the olefin polymer production, compressing pressures of respective gas components in the exhaust gas to a same level, and outputting a high pressure gas stream;

the first heat exchanger is used for receiving and cooling the high pressure gas stream from the compressor and outputting a gas-liquid mixture having a temperature lower than a dew point temperature of the high pressure gas stream; and in some specific embodiments of the present invention, the first heat exchanger is a tubular heat exchanger which cools a compressed high pressure gas stream to a low temperature as much as possible by using an inexpensive cold medium, such as circulating cooling water, so as to save energy consumption of a subsequent mechanism; and a gas phase outlet of the first gas-liquid separator is connected to the first outlet of the compression cooling mechanism, and a liquid phase outlet thereof is connected to a second outlet of the compression cooling mechanism; and the first gas-liquid separator is used for receiving the gas-liquid mixture and performing gas-liquid separation, and then outputting the recycled $C_4^+$ high carbon hydrocarbon stream via a liquid phase outlet and outputting the remaining exhaust gas stream via a gas phase outlet, the remaining exhaust gas stream entering the hydrocarbon membrane separation mechanism and the hydrogen membrane separation mechanism. A volume ratio of a remaining exhaust gas stream entering the hydrocarbon membrane separation mechanism to a remaining exhaust gas stream entering the hydrogen membrane separation mechanism is 0.1 to 0.8; preferably, the volume ratio of the remaining exhaust gas stream entering the hydrocarbon membrane separation mechanism to the remaining exhaust gas stream entering the hydrogen membrane separation mechanism is 0.4 to 0.6; further preferably, the volume ratio of the remaining exhaust gas stream entering the hydrocarbon membrane separation mechanism to the remaining exhaust gas stream entering the hydrogen membrane separation mechanism is 0.45 to 0.55; and even more preferably, the volume ratio of the remaining exhaust gas stream entering the hydrocarbon membrane separation mechanism to the remaining exhaust gas stream entering the hydrogen membrane separation mechanism is 0.5.

In other embodiments of the present invention, an inlet of the hydrocarbon membrane separation mechanism is connected to the first outlet of the compression cooling mechanism, and a first outlet of the hydrocarbon membrane separation mechanism is connected to the inlet of the compression cooling mechanism. The hydrocarbon membrane separation mechanism comprises at least one hydrocarbon membrane module for receiving the remaining exhaust gas stream. A $C_4^+$ high carbon hydrocarbon stream outputted at a permeate side of the hydrocarbon membrane module is returned to the compression cooling mechanism, and the PDS transport gas stream outputted at a retentate side of the hydrocarbon membrane module is transported as a PDS transport gas to an upstream polyolefin powder discharge device.

In some embodiments of the present invention, an inlet of the hydrogen membrane separation mechanism is connected to the first outlet of the compression cooling mechanism, and the first outlet of the hydrogen membrane separation mechanism is connected to an inlet of the deep cooling mechanism. The hydrogen membrane separation mechanism comprises at least one hydrogen membrane module for receiving a remaining exhaust gas stream. A mixed non-condensable gas stream containing a hydrogen gas is outputted at a permeate side of the hydrogen membrane module and is discharged to a flare system, and the remaining tail gas stream is outputted at a retentate side of the hydrogen membrane module. In some specific embodiments of the invention, the mixed non-condensable gas stream containing the hydrogen gas comprises a non-condensable gas, such as a hydrogen gas, a nitrogen gas, methane and so on, and generally has a composition that can still satisfy heat value requirements of a fuel gas.

In other embodiments of the present invention, the deep cooling mechanism comprises at least one deep cooling unit, and the deep cooling unit comprises a second heat exchanger, a second gas-liquid separator, a first throttle valve, a third heat exchanger, a third gas-liquid separator, a second throttle valve, a turbo expander, and a turbo expander pressurization end.

The second heat exchanger is used for receiving and cooling a remaining tail gas stream from the hydrogen membrane separation mechanism and outputting a first gas-liquid mixture;

the second gas-liquid separator is used for receiving the first gas-liquid mixture and performing gas-liquid separation, outputting a first liquid phase stream via a liquid phase outlet, and outputting a first gas phase stream via a gas phase outlet; and the first liquid phase stream, after flowing through the first throttle valve, is returned to the second heat exchanger, and after a heat exchange is performed, a $C_4^+$ high carbon hydrocarbon stream outputted is returned to the compression cooling mechanism so as to provide cooling capacity to the second heat exchanger;

the third heat exchanger is used for receiving and cooling the first gas phase stream and outputting a second gas-liquid mixture;

the third gas-liquid separator is used for receiving the second gas-liquid mixture and performing gas-liquid separation, outputting a second liquid phase stream via a liquid phase outlet, and outputting a second gas phase stream via a gas phase outlet;

the second liquid phase stream, after flowing through the second throttle valve, is returned to the third heat exchanger, and after an heat exchange is performed, the second liquid phase stream is returned to the second heat exchanger, and a nitrogen gas stream is outputted, so as to provide cooling capacity to the second heat exchanger and the third heat exchanger; and the second gas phase stream, after being returned to the third heat exchanger for a heat exchange, enters the turbo expander; after being processed, the second gas phase stream is returned to the third heat exchanger again for a second heat exchange, and then is sent to the second heat exchanger; finally after a heat exchange is performed in the second heat exchanger and cooling capacity is provided to the second heat exchanger, the second gas phase stream enters the turbo expander pressurization end; and after a processing is performed, the $C_2^+$ low carbon hydrocarbon stream is outputted and sent to an upstream polyolefin powder degassing device for use.

According to the present invention, when the deep cooling mechanism comprises one deep cooling unit, a first inlet of the second heat exchanger is connected to an inlet of the deep cooling mechanism, and a first outlet of the second heat exchanger is connected to an inlet of the second gas-liquid separator, a gas phase outlet of the second gas-liquid separator being connected to a first inlet of the third heat exchanger, a first outlet of the third heat exchanger being connected to an inlet of the third gas-liquid separator, a gas phase outlet of the third gas-liquid separator being connected to a second inlet of the third heat exchanger, a second outlet of the third heat exchanger being connected to an inlet of the turbo expander, an outlet of the turbo expander being connected to a third inlet of the third heat exchanger, a third outlet of the third heat exchanger being connected to a fourth inlet of the second heat exchanger, a fourth outlet of the second heat exchanger being connected to an inlet of the turbo expander pressurization end, an outlet of the turbo expander pressurization end being connected to a second outlet of the deep cooling mechanism;

a liquid phase outlet of the second gas-liquid separator is connected to an inlet of the first throttle valve, and an outlet of the first throttle valve is connected to a second inlet of the second heat exchanger, a second outlet of the second heat exchanger being connected to an inlet of the compression cooling mechanism; and a liquid phase outlet of the third gas-liquid separator is connected to an inlet of the second throttle valve, and an outlet of the second throttle valve is connected to a fourth inlet of the third heat exchanger, a fourth outlet of the third heat exchanger being connected to a third inlet of the second heat exchanger, a third outlet of the second heat exchanger being connected to a first outlet of the deep cooling mechanism.

In some embodiments of the invention, the second heat exchanger and the third heat exchanger are tubular heat exchangers or plate heat exchangers, preferably plate heat exchangers. Since a plate heat exchanger can be used to simultaneously exchange heat of multiple streams, using the plate heat exchanger can significantly reduce equipment investment and energy loss when cooling capacity of the deep cooling mechanism is recycled.

In other embodiments of the present invention, in the deep cooling unit, an expansion ratio of the first throttle valve and an expansion ratio of the second throttle valve are both 5.0 to 20.0; and preferably the expansion ratio of the first throttle valve and the expansion ratio of the second throttle valve are both 6.0 to 16.0 so as to obtain sufficient cooling capacity to ensure stable operation of the deep cooling mechanism.

In still other embodiments of the invention, an expansion ratio of the turbo expander is 1.6 to 10.0; and preferably the expansion ratio of the turbo expander is 2.5 to 5.0.

According to the invention, cooling mediums used in the system are all mediums having a temperature not lower than an ambient temperature.

A method for recycling an exhaust gas in olefin polymer production by using a system as described in the first aspect is provided according to the second aspect. The method comprises:

a compression cooling step, wherein after an olefin polymer exhaust gas is fed into a compression cooling mechanism, the olefin polymer exhaust gas is processed by a compression cooling unit to form a remaining exhaust gas stream which is outputted via a first outlet of the compression cooling mechanism, and a $C_4^+$ high carbon hydrocarbon stream as a liquid phase which is outputted via a second outlet of the compression cooling mechanism, and the remaining exhaust gas stream is fed into a hydrocarbon membrane separation mechanism;

a hydrocarbon membrane separation step, wherein the remaining exhaust gas stream fed into the hydrocarbon membrane separation mechanism is processed by a hydrocarbon membrane module to form a product discharge system (PDS) transport gas stream which is outputted via a first outlet of the hydrocarbon membrane separation mechanism, and a $C_4^+$ high carbon hydrocarbon stream which is outputted via a second outlet of the hydrocarbon membrane separation mechanism, and the remaining exhaust gas is fed into a hydrogen membrane separation mechanism;

a hydrogen membrane separation step, wherein the remaining exhaust gas fed into the hydrogen membrane separation mechanism is processed by a hydrogen membrane module to form a remaining tail gas stream which is outputted via a first outlet of the hydrogen membrane separation mechanism, and a mixed non-condensable gas stream containing hydrogen gas which is outputted via a second outlet of the hydrogen membrane separation mechanism, and the remaining tail gas stream is fed into a deep cooling mechanism; and a deep cooling step, wherein the remaining tail gas stream fed into the deep cooling mechanism is processed by a deep cooling unit to form a nitrogen gas stream which is outputted via a first outlet of the deep cooling mechanism, a $C_2^+$ low carbon hydrocarbon stream which is outputted via a second outlet of the deep cooling mechanism, and a $C_4^+$ high carbon hydrocarbon stream which is outputted via a third outlet of the deep cooling mechanism.

In some embodiments of the invention, a volume ratio of the remaining exhaust gas stream fed into the hydrocarbon membrane separation mechanism to the remaining exhaust gas stream fed into the hydrogen membrane separation mechanism is 0.1 to 0.8; preferably, the volume ratio of the remaining exhaust gas stream fed into the hydrocarbon membrane separation mechanism to the remaining exhaust gas stream fed into the hydrogen membrane separation mechanism is 0.4 to 0.6; further preferably, the volume ratio of the remaining exhaust gas stream fed into the hydrocarbon membrane separation mechanism to the remaining exhaust gas stream fed into the hydrogen membrane separation mechanism is 0.45 to 0.55; and even more preferably, the volume ratio of the remaining exhaust gas stream fed into the hydrocarbon membrane separation mechanism to the remaining exhaust gas stream fed into the hydrogen membrane separation mechanism is 0.5.

In other embodiments of the present invention, the $C_4^+$ high carbon hydrocarbon stream outputted via the second outlet of the hydrocarbon membrane separation mechanism is returned to the compression cooling mechanism.

In still other embodiments of the present invention, the $C_4^+$ high carbon hydrocarbon stream outputted via the third outlet of the deep cooling mechanism is returned to the compression cooling mechanism.

In the present invention, the term "$C_4^+$ high carbon hydrocarbon stream" means a material stream in which a total content of $C_4$ component, $C_5$ component and $C_6$ component is higher than a total content of $C_2$ component and $C_1$ component; and the term "$C_2^+$ low carbon hydrocarbon stream" means a material stream in which a total content of $C_2$ component and $C_1$ component is higher than a total content of $C_4$ component, $C_5$ component and $C_6$ component.

Embodiment

For better understanding of the present invention, the present invention will be further described in detail below with reference to the drawings in combination with embodiments. The embodiments are used for illustration only, not for limiting the application scope of the present invention. Raw materials or components used in the present invention can be obtained by a commercial manner or prepared by a conventional method unless otherwise specified.

The FIGURE schematically shows a system used to effectively recycle respective components of an exhaust gas during olefin polymer production used in the present embodiment, and the system comprises:

a compression cooling mechanism 101;

a hydrocarbon membrane separation mechanism 102 and a hydrogen membrane separation mechanism 103, both connected to a first outlet 202 of the compression cooling mechanism; and a deep cooling mechanism 104 connected to a first outlet 208 of the hydrogen membrane separation mechanism.

The compression cooling mechanism 101 comprises two compression cooling units connected in series, i.e., a front compression cooling unit and a rear compression cooling unit. The front compression cooling unit comprises a front compressor 1011, a front first heat exchanger 1012, and a front first gas-liquid separator 1013. The rear compression cooling unit comprises a rear compressor 1014, a rear first heat exchanger 1015, and a rear first gas-liquid separator 1016. The compression cooling mechanism 101 is used for receiving an exhaust gas 1, compressing pressures of respective gas components in the exhaust gas 1 to a same level, and respectively outputting a $C_4^+$ high carbon hydrocarbon stream 2' recycled by the front compression cooling unit, a $C_4^+$ high carbon hydrocarbon stream 2" recycled by the rear compression cooling unit, and a third stream 3 (a remaining exhaust gas).

The hydrocarbon membrane separation mechanism 102 comprises a hydrocarbon membrane separation module 1021, and is used for controlling a content of $C_4^+$ high carbon hydrocarbon in a seventh stream 7 (a PDS transport gas stream).

The hydrogen membrane separation mechanism 103 comprises a hydrogen membrane separation module 1031, and is used for controlling a content of a hydrogen gas component in a ninth stream 9 (a remaining tail gas stream).

The deep cooling mechanism comprises one deep cooling unit. The deep cooling unit comprises a second heat exchanger 1041, a second gas-liquid separator 1042, a first throttle valve 1043, a third heat exchanger 1044, a third gas-liquid separator 1045, a second throttle valve 1046, a turbo expander 1047, and a turbo expander pressurization end 1048. The deep cooling mechanism is used for receiving the ninth stream 9 (the remaining tail gas stream) from the hydrogen membrane separation mechanism 103 and respectively recycling a twenty-fifth stream 25 (a $C_2^+$ low carbon hydrocarbon stream) and a ninth stream 19 (a nitrogen gas stream).

An inlet 201 of the compression cooling mechanism 101 is connected to an inlet 301 of the front compressor 1011. An outlet 302 of the front compressor 1011 is connected to an inlet 303 of the front first heat exchanger 1012. An outlet 304 of the front first heat exchanger 1012 is connected to an inlet 305 of the front first gas-liquid separator 1013. A liquid phase outlet 307 of the front first gas-liquid separator 1013 is connected to a front second outlet 2031 of the compression cooling mechanism 101, and a gas phase outlet 306 thereof is connected to an inlet 308 of the rear compressor 1014. An outlet 309 of the rear compressor 1014 is connected to an inlet 310 of the rear first heat exchanger 1015. An outlet 311 of the rear first heat exchanger 1015 is connected to an inlet 312 of the rear first gas-liquid separator 1016. A liquid phase outlet 314 of the rear first gas-liquid separator 1016 is connected to a rear second outlet 2032 of the compression cooling mechanism 101, and a gas phase outlet 313 thereof is connected to the first outlet 202 of the compression-cooling mechanism 101.

The first outlet 202 of the compression cooling mechanism 101 is connected to both an inlet 204 of the hydrocarbon membrane separation mechanism 102 and an inlet 207 of the hydrogen membrane separation mechanism 103. A first outlet 205 of the hydrocarbon membrane separation mechanism 102 is used for outputting the seventh stream 7 (a PDS transport stream), and a second outlet 206 of the hydrocarbon membrane separation mechanism 102 is connected to the inlet 201 of the compression cooling mechanism 101. A second outlet 209 of the hydrogen membrane separation mechanism 103 is used for outputting an eighth stream 8 (a mixed non-condensable gas stream containing a hydrogen gas), and a first outlet 208 of the hydrogen membrane separation mechanism 103 is connected to an inlet 210 of the deep cooling mechanism 104.

A first inlet 4011 of the second heat exchanger 1041 is connected to the inlet 210 of the deep cooling mechanism 104, and a first outlet 4012 of the second heat exchanger 1041 is connected to an inlet 214 of the second gas-liquid separator 1042. A gas phase outlet 216 of the second gas-liquid separator 1042 is connected to a first inlet 4051 of the third heat exchanger 1044. A first outlet 4052 of the third heat exchanger 1044 is connected to an inlet 217 of the third gas-liquid separator 1045. A gas phase outlet 219 of the third gas-liquid separator 1045 is connected to a second inlet 4061 of the third heat exchanger 1045. A second outlet 4062 of the third heat exchanger 1045 is connected to an inlet 227 of the turbo expander 1047. An outlet 220 of the turbo expander 1047 is connected to a third inlet 4071 of the third heat exchanger 1044. A third outlet 4072 of the third heat exchanger 1044 is connected to a fourth inlet 4041 of the second heat exchanger 1041. A fourth outlet 4042 of the second heat exchanger 1041 is connected to an inlet 221 of the turbo expander pressurization end 1048. An outlet 226 of the turbo expander pressurization end 1048 is connected to a second outlet 212 of the deep cooling mechanism 104.

A liquid phase outlet 215 of the second gas-liquid separator 1042 is connected to an inlet 222 of the first throttle valve 1043. An outlet 223 of the first throttle valve 1043 is connected to a second inlet 4021 of the second heat exchanger 1041. A second outlet 4022 of the second heat exchanger 1041 is connected to the inlet 201 of the compression cooling mechanism 101 via a third outlet 213 of the deep cooling mechanism 104.

A liquid phase outlet 218 of the third gas-liquid separator 1045 is connected to an inlet 224 of the second throttle valve 1046. An outlet 225 of the second throttle valve 1046 is connected to a fourth inlet 4081 of the third heat exchanger 1044. A third outlet 4082 of the third heat exchanger 1044 is connected to a fourth inlet 4031 of the second heat exchanger 1041. A third outlet 4032 of the second heat exchanger 1041 is connected to a first outlet 211 of the deep cooling mechanism 104.

The front compressor 1011 and the rear compressor 1014 are both reciprocating compressors, and the front first heat exchanger 1012 and the rear first heat exchanger 1015 are both fixed tube-plate heat exchangers.

The front first heat exchanger 1012 and the rear first heat exchanger 1015 function to use a cold medium having a temperature not lower than an ambient temperature, such as circulating cooling water, to cool a compressed exhaust gas to a temperature as low as possible, so as to save energy consumption of a subsequent mechanism.

The second heat exchanger 1041 and the third heat exchanger 1044 are tubular heat exchangers or plate heat exchangers, preferably plate heat exchangers. Since a plate heat exchanger can be used to simultaneously exchange heat of multiple streams, using the plate heat exchanger can significantly reduce equipment investment and energy loss when cooling capacity of the deep cooling mechanism is recycled.

The method for recycling an exhaust gas in olefin polymer production by using the system may comprises the following steps.

(1) A Compression Cooling Step

An exhaust gas 1 from the olefin polymer production flows via an inlet 201 of a compression cooling mechanism 101. After being pressurized to 0.4 MPaA by a front compressor 1011, the exhaust gas 1 is then cooled to 35° C. by a front first heat exchanger 1012 to form a cooled high-pressure gas which is fed into a front first gas-liquid separator 1013 for gas-liquid separation. A $C_4^+$ high carbon hydrocarbon stream 2' recycled by a front compression cooling unit is outputted via a liquid phase outlet 307, and is discharged via a front second outlet 2031 of the front compression-cooling mechanism 101. After a gas stream from a gas phase outlet 306 of the first gas-liquid separator 1013 is sent into a rear compressor 1014 to be pressurized to 1.7 MPaA, the gas stream is cooled to 37° C. by a rear first heat exchanger 1015 and is fed into a rear first gas-liquid separator 1016. A $C_4^+$ high carbon hydrocarbon stream 2" recycled by a rear compression cooling unit is outputted via a liquid phase outlet 314, and is discharged via a rear second outlet 2032 of the compression cooling mechanism 101. A third stream 3 (a remaining exhaust gas stream) is outputted via a gas phase outlet 313, and is discharged via a first outlet 202 of the compression cooling mechanism 101. The third stream 3 (the remaining exhaust gas stream) discharged from the compression cooling mechanism is separated into a fourth stream 4 and a fifth stream 5, and a separation rate thereof is 50%.

(2) a Hydrocarbon Membrane Separation Step

The fifth stream 5 is fed into a hydrocarbon membrane separation mechanism 102 via an inlet 204 of the hydrocarbon membrane separation mechanism 102. After the fifth stream 5 is processed by a hydrocarbon membrane module, a sixth stream 6 (a $C_4^+$ high carbon hydrocarbon stream recycled by the hydrocarbon membrane module) is outputted at a permeate side of the hydrocarbon membrane module, and the sixth stream 6 is returned to the compression cooling mechanism 101; and a seventh stream 7 (a PDS transport gas stream) is outputted at a retentate side of the hydrocarbon membrane module, and the seventh stream 7 is sent to an upstream polyolefin powder discharge device.

(3) a Hydrogen Membrane Separation Step

A fourth stream 4 is fed into a hydrogen membrane separation mechanism 103 via an inlet 207 thereof. After the fourth stream 4 is processed by a hydrogen membrane module, an eighth stream 8 (a mixed non-condensable gas stream containing hydrogen gas) is outputted at a permeate side of the hydrogen membrane module and is discharged to a flare system, and a ninth stream 9 (a remaining exhaust gas stream) is outputted at a retentate side of the hydrogen membrane module.

(4) a Deep Cooling Step

The ninth stream 9 (the remaining exhaust gas stream) is fed into a deep cooling mechanism 104 via a first inlet 210 of the deep cooling mechanism 104, and is fed into a second heat exchanger 1041 via a first inlet 4011 of the second heat exchanger 1041. After a heat exchange is performed, a tenth stream 10 (a first gas-liquid mixture) obtained is outputted via a first outlet 4012 of the second heat exchanger 1041. The tenth stream 10 has a temperature of −55° C. and a pressure of 1.68 MPaA. The tenth stream 10 is fed into a second gas-liquid separation tank 1042 via an inlet 214 of the second gas-liquid separation tank 1042 for gas-liquid separation. A twelfth stream 12 (a first liquid phase stream) is outputted via a liquid phase outlet 215, and an eleventh stream 11 (a first gas phase stream) is outputted via a gas phase outlet 216.

The eleventh stream 11 is fed into a third heat exchanger 1044 via a first inlet 4051 thereof for a first heat exchange, and a fifteenth stream 15 (a second gas-liquid mixture) is outputted via a first outlet 4052 of the third heat exchanger 1044. The fifteenth stream 15 has a temperature of −120° C. and a pressure of 1.67 MPaA. The fifteenth stream 15 is fed into a third gas-liquid separator 1045 via an inlet 217 thereof for gas-liquid separation. A sixteenth stream 16 (a second liquid phase stream) is outputted via a liquid phase outlet 218, and a twentieth stream 20 (a second gas phase stream) is outputted via a gas phase outlet 219.

The twentieth stream 20 is returned to the third heat exchanger 1044 via a second inlet 4061 thereof, and a first heat exchange is performed. After that, a twenty-first stream 21 is outputted via a second outlet 4062 of the third heat exchanger 1044. The twenty-first stream 21 has a temperature of −90° C. and a pressure of 1.66 MPaA. The twenty-first stream 21 is fed into a turbo expander 1047, and after the twenty-first stream 21 is processed, a twenty-second stream 22 is outputted. The twenty-second stream 22 has a temperature of −139° C. and a pressure of 0.30 MPaA. The twenty-second stream 22 is returned to the third heat exchanger 1044 via a third inlet 4071 thereof, and a second heat exchange is performed. After that, a twenty-third stream 23 is outputted. The twenty-third stream 23 has a temperature of −83° C. and a pressure of 0.29 MPaA. The twenty-third stream 23 is fed into the second heat exchanger 1041 via a fourth inlet 4041 of the second heat exchanger 1041, and after a heat exchange is performed by the second heat exchanger 1041, a twenty-fourth stream 24 is outputted. The twenty-fourth stream 24 has a temperature of 31° C. and a pressure of 0.285 MPaA. After the twenty-fourth stream 24 is processed by a turbo expander pressurization end 1048, a twenty-fifth stream 25 (a $C_2^+$ low carbon stream) is outputted, and the twenty-fifth stream 25 is sent to an upstream polyolefin powder degassing device for use. The turbo expander 1047 has an expansion ratio of 1.6 to 10.0, preferably 2.5 to 5.0.

The twelfth stream 12 is fed into a first throttle valve 1043. After the twelfth stream 12 is processed by the first throttle valve 1043, a thirteenth stream 13 is outputted. The thirteenth stream 13 has a temperature of −61° C. and a pressure of 0.13 MPaA. The thirteen stream 13 is fed into the second heat exchanger 1041 via a second inlet 4021 thereof. After a heat exchange is performed, a fourteenth stream 14 (a $C_4^+$ high carbon hydrocarbon stream) is outputted via a second outlet 4022 of the second heat exchanger 1041. The fourteen stream 14 has a temperature of 31° C. and a pressure of 0.13 MPaA. The fourteen stream 14 is outputted via a third outlet 213 of the deep cooling mechanism and is returned to the inlet 201 of the compression mechanism 101 so as to provide cooling capacity for the second heat exchanger 1041. The first throttle valve 1043 has an expansion ratio of 5.0 to 20.0, preferably 6.0 to 16.0, to obtain sufficient cooling capacity so as to ensure stable operation of the deep cooling mechanism.

The sixteenth stream 16 is fed into a second throttle valve 1046. After the sixteenth stream 16 is processed by the second throttle valve 1046, a seventeenth stream 17 is outputted. The seventeenth stream 17 has a temperature of −123° C. and a pressure of 0.32 MPaA. The seventeenth stream 17 is returned to the third heat exchanger 1044 via a fourth inlet 4081 of the third heat exchanger 1044 for a heat exchange. After that, an eighteenth stream 18 is outputted via a fourth outlet 4082 of the third heat exchanger 1044. The eighteenth stream 18 has a temperature of −83° C. and a pressure of 0.31 MPaA. The eighteenth stream 18 is returned to the second heat exchanger 1041 via a third inlet 4031 of the second heat exchanger 1041 for a heat exchange. After that, a nineteenth stream 19 (a nitrogen gas stream) is outputted via a third outlet 4032 of the second heat exchanger 1041. The nineteenth stream 19 has a temperature of 31° C. and a pressure of 0.3 MPaA. The nineteenth stream 19 is outputted via a first outlet 211 of the deep cooling mechanism so as to provide cooling capacity to the second heat exchanger 1041 and the third heat exchanger 1044. The second throttle valve 1046 has an expansion ratio of 5.0 to 20.0, preferably 6.0 to 16.0 to provide obtain sufficient cooling capacity so as to ensure stable operation of the deep cooling mechanism.

The second heat exchanger 1041 functions to cool the ninth stream 9 fed into the second heat exchanger 1041 via the first inlet 4011 of the second exchanger 1041 to a temperature below a dew point so as to obtain the tenth stream 10 (the first gas-liquid mixture). The third heat exchanger 1044 functions to cool the eleventh stream 11 fed into the third heat exchanger 1044 via the first inlet 4051 of the third heat exchanger 1044 to a temperature below a dew point so as to obtain the fifteenth stream 15 (the second gas-liquid mixture).

In the example of the present invention, the eighth stream 8 comprises a non-condensable gas, such as hydrogen gas, nitrogen gas, methane and so on, and has a composition that can still satisfy heat value requirements of a fuel gas.

It should be noted that the above embodiments are only for explaining the present invention and do not constitute any limitation to the present invention. The present invention is described with reference to preferred embodiments thereof, but it should be understood words used therein are descriptive and explanatory, rather than restrictive. The present invention may be modified within the scope of the claims, and the present invention may be modified without departing from the scope and spirit of the present invention. Although the present invention is described in terms of specific methods, materials, and embodiments, it does not mean that the invention is limited to the specific examples disclosed herein. Instead, the present invention can be extended to all other methods and applications having the same function.

The invention claimed is:

1. A system for recycling an exhaust gas in olefin polymer production, comprising:
a compression cooling mechanism;
a hydrocarbon membrane separation mechanism and a hydrogen membrane separation mechanism, both connected to a first outlet of the compression cooling mechanism; and
a deep cooling mechanism connected to a first outlet of the hydrogen membrane separation mechanism,
wherein, the deep cooling mechanism is used for receiving the remaining tail gas stream from the hydrogen membrane separation mechanism and recycling a $C_2^+$ low carbon hydrocarbon stream and a nitrogen gas stream,
the deep cooling mechanism comprises at least one deep cooling unit, wherein the deep cooling unit comprises a second heat exchanger, a second gas-liquid separator, a first throttle valve, a third heat exchanger, a third gas-liquid separator, a second throttle valve, a turbo expander, and a turbo expander pressurization end.

2. The system according to claim 1, wherein the compression cooling mechanism comprises at least one compression cooling unit, wherein the compression cooling unit comprises a compressor, a first heat exchanger, and a first gas-liquid separator, wherein the compressor, the first heat exchanger, and the first gas-liquid separator are connected in series.

3. The system according to claim 1, wherein the deep cooling mechanism comprises one deep cooling unit,
wherein a first inlet of the second heat exchanger is connected to an inlet of the deep cooling mechanism, a first outlet of the second heat exchanger is connected to an inlet of the second gas-liquid separator, a gas phase outlet of the second gas-liquid separator is connected to a first inlet of the third heat exchanger, a first outlet of the third heat exchanger is connected to an inlet of the third gas-liquid separator, a gas phase outlet of the third gas-liquid separator is connected to a second inlet of the third heat exchanger, a second outlet of the third heat exchanger is connected to an inlet of the turbo expander, an outlet of the turbo expander is connected to a third inlet of the third heat exchanger, a third outlet of the third heat exchanger is connected to a fourth inlet of the second heat exchanger, a fourth outlet of the second heat exchanger is connected to an inlet of the turbo expander pressurization end, and an outlet of the turbo expander pressurization end is connected to a second outlet of the deep cooling mechanism;
a liquid phase outlet of the second gas-liquid separator is connected to an inlet of the first throttle valve, and an outlet of the first throttle valve is connected to a second inlet of the second heat exchanger, a second outlet of the second heat exchanger being connected to an inlet of the compression cooling mechanism; and
a liquid phase outlet of the third gas-liquid separator is connected to an inlet of the second throttle valve, and an outlet of the second throttle valve is connected to a fourth inlet of the third heat exchanger, a fourth outlet of the third heat exchanger being connected to a third inlet of the second heat exchanger, a third outlet of the second heat exchanger being connected to a first outlet of the deep cooling mechanism.

4. The system according to claim 2, wherein when the deep cooling mechanism comprises one deep cooling unit,
a first inlet of the second heat exchanger is connected to an inlet of the deep cooling mechanism, and a first outlet of the second heat exchanger is connected to an inlet of the second gas-liquid separator, a gas phase outlet of the second gas-liquid separator being connected to a first inlet of the third heat exchanger, a first outlet of the third heat exchanger being connected to an inlet of the third gas-liquid separator, a gas phase outlet of the third gas-liquid separator being connected to a second inlet of the third heat exchanger, a second outlet of the third heat exchanger being connected to an inlet of the turbo expander, an outlet of the turbo expander being connected to a third inlet of the third heat exchanger, a third outlet of the third heat exchanger being connected to a fourth inlet of the second heat exchanger, a fourth outlet of the second heat exchanger being connected to an inlet of the turbo expander pressurization end, an outlet of the turbo expander pressurization end being connected to a second outlet of the deep cooling mechanism;
a liquid phase outlet of the second gas-liquid separator is connected to an inlet of the first throttle valve, and an outlet of the first throttle valve is connected to a second inlet of the second heat exchanger, a second outlet of the second heat exchanger being connected to an inlet of the compression cooling mechanism; and
a liquid phase outlet of the third gas-liquid separator is connected to an inlet of the second throttle valve, and an outlet of the second throttle valve is connected to a fourth inlet of the third heat exchanger, a fourth outlet of the third heat exchanger being connected to a third inlet of the second heat exchanger, a third outlet of the second heat exchanger being connected to a first outlet of the deep cooling mechanism.

5. The system according to claim 1, wherein a second outlet of the hydrocarbon membrane separation mechanism is connected to an inlet of the compression cooling mechanism.

6. The system according to claim 1, wherein cooling mediums used in the system all have a temperature not lower than an ambient temperature.

7. A method for recycling an exhaust gas in olefin polymer production comprising:
a compression cooling step, wherein after an olefin polymer exhaust gas is fed into a compression cooling mechanism, the olefin polymer exhaust gas is processed by a compression cooling unit to form a remaining exhaust gas stream which is outputted via a first outlet of the compression cooling mechanism, and a $C_4^+$ high carbon hydrocarbon stream as a liquid phase which is outputted via a second outlet of the compression cooling mechanism, and the remaining exhaust gas stream is fed into a hydrocarbon membrane separation mechanism;

a hydrocarbon membrane separation step, wherein the remaining exhaust gas stream fed into the hydrocarbon membrane separation mechanism is processed by a hydrocarbon membrane module to form a product discharge system (PDS) transport gas stream which is outputted via a first outlet of the hydrocarbon membrane separation mechanism, and a $C_4^+$ high carbon hydrocarbon stream which is outputted via a second outlet of the hydrocarbon membrane separation mechanism, and the remaining exhaust gas is fed into a hydrogen membrane separation mechanism;

a hydrogen membrane separation step, wherein the remaining exhaust gas fed into the hydrogen membrane separation mechanism is processed by a hydrogen membrane module to form a remaining tail gas stream which is outputted via a first outlet of the hydrogen membrane separation mechanism, and a mixed non-condensable gas stream containing hydrogen gas which is outputted via a second outlet of the hydrogen membrane separation mechanism, and the remaining tail gas stream is fed into a deep cooling mechanism; and a deep cooling step, wherein the remaining tail gas stream fed into the deep cooling mechanism is processed by a deep cooling unit to form a nitrogen gas stream which is outputted via a first outlet of the deep cooling mechanism, a $C_2^+$ low carbon hydrocarbon stream which is outputted via a second outlet of the deep cooling mechanism, and a $C_4^+$ high carbon hydrocarbon stream which is outputted via a third outlet of the deep cooling mechanism, wherein, the deep cooling mechanism is used for receiving the remaining tail gas stream from the hydrogen membrane separation mechanism and recycling a $C_2^+$ low carbon hydrocarbon stream and a nitrogen gas stream, the deep cooling mechanism comprises at least one deep cooling unit, wherein the deep cooling unit comprises a second heat exchanger, a second gas-liquid separator, a first throttle valve, a third heat exchanger, a third gas-liquid separator, a second throttle valve, a turbo expander, and a turbo expander pressurization end.

8. The method according to claim 7, wherein the $C_4^+$ high carbon hydrocarbon stream outputted via the second outlet of the hydrocarbon membrane separation mechanism is returned to the compression cooling mechanism.

9. The method according to claim 7, wherein the $C_4^+$ high carbon hydrocarbon stream outputted via the third outlet of the deep cooling mechanism is returned to the compression cooling mechanism.

10. The method according to claim 8, wherein the $C_4^+$ high carbon hydrocarbon stream outputted via the third outlet of the deep cooling mechanism is returned to the compression cooling mechanism.

11. The method according to claim 7, wherein a volume ratio of the remaining exhaust gas stream fed into the hydrocarbon membrane separation mechanism to the remaining exhaust gas stream fed into the hydrogen membrane separation mechanism is 0.1 to 0.8.

12. The method according to claim 7, wherein the $C_4^+$ high carbon hydrocarbon stream outputted via the second outlet of the hydrocarbon membrane separation mechanism is returned to the compression cooling mechanism.

13. The method according to claim 7, wherein the $C_4^+$ high carbon hydrocarbon stream outputted via the third outlet of the deep cooling mechanism is returned to the compression cooling mechanism.

14. The method according to claim 7, wherein the compression cooling mechanism comprises at least one compression cooling unit, wherein the compression cooling unit comprises a compressor, a first heat exchanger, and a first gas-liquid separator, wherein the compressor, the first heat exchanger, and the first gas-liquid separator are connected in series.

15. The method according to claim 7, wherein when the deep cooling mechanism comprises one deep cooling unit, a first inlet of the second heat exchanger is connected to an inlet of the deep cooling mechanism, and a first outlet of the second heat exchanger is connected to an inlet of the second gas-liquid separator, a gas phase outlet of the second gas-liquid separator being connected to a first inlet of the third heat exchanger, a first outlet of the third heat exchanger being connected to an inlet of the third gas-liquid separator, a gas phase outlet of the third gas-liquid separator being connected to a second inlet of the third heat exchanger, a second outlet of the third heat exchanger being connected to an inlet of the turbo expander, an outlet of the turbo expander being connected to a third inlet of the third heat exchanger, a third outlet of the third heat exchanger being connected to a fourth inlet of the second heat exchanger, a fourth outlet of the second heat exchanger being connected to an inlet of the turbo expander pressurization end, an outlet of the turbo expander pressurization end being connected to a second outlet of the deep cooling mechanism;

a liquid phase outlet of the second gas-liquid separator is connected to an inlet of the first throttle valve, and an outlet of the first throttle valve is connected to a second inlet of the second heat exchanger, a second outlet of the second heat exchanger being connected to an inlet of the compression cooling mechanism; and a liquid phase outlet of the third gas-liquid separator is connected to an inlet of the second throttle valve, and an outlet of the second throttle valve is connected to a fourth inlet of the third heat exchanger, a fourth outlet of the third heat exchanger being connected to a third inlet of the second heat exchanger, a third outlet of the second heat exchanger being connected to a first outlet of the deep cooling mechanism.

16. The method according to claim 11, wherein the volume ratio of the remaining exhaust gas stream fed into the hydrocarbon membrane separation mechanism to the remaining exhaust gas stream fed into the hydrogen membrane separation mechanism is 0.4 to 0.6.

17. The method according to claim 11, wherein the volume ratio of the remaining exhaust gas stream fed into the hydrocarbon membrane separation mechanism to the remaining exhaust gas stream fed into the hydrogen membrane separation mechanism is 0.45 to 0.55.

* * * * *